(12) United States Patent
Nakamura et al.

(10) Patent No.: US 6,508,651 B1
(45) Date of Patent: Jan. 21, 2003

(54) DENTURES AND FALSE TEETH

(75) Inventors: Shoji Nakamura, Takahama (JP); Hideyasu Tamagawa, Nagoya (JP)

(73) Assignee: Yamaguchi Shizai Kogyo Kabushiki Kaisha, Aichi (JP)

( * ) Notice: Subject to any disclaimer, the term of this patent is extended or adjusted under 35 U.S.C. 154(b) by 0 days.

(21) Appl. No.: 09/711,853

(22) Filed: Nov. 13, 2000

(30) Foreign Application Priority Data

Nov. 11, 1999 (JP) ............................................ 11-321474
Apr. 21, 2000 (JP) ....................................... 2000-121439

(51) Int. Cl.$^7$ ............................................. A61C 13/08
(52) U.S. Cl. ..................................................... 433/197
(58) Field of Search ................................. 433/196, 197, 433/202.1, 212.1

(56) References Cited

U.S. PATENT DOCUMENTS

| | | | | |
|---|---|---|---|---|
| 1,878,517 A | * | 9/1932 | Hiltebrandt | 433/197 |
| 2,195,370 A | * | 3/1940 | La Due et al. | 433/197 |
| 2,620,562 A | * | 12/1952 | Folsom | 433/197 |
| 2,708,314 A | * | 5/1955 | Schwartz | 433/197 |
| 3,252,220 A | * | 5/1966 | Goddard | 433/197 |
| 3,456,347 A | * | 7/1969 | Spinella | 433/196 |
| 3,638,309 A | * | 2/1972 | Frush | 433/197 |
| 4,208,794 A | * | 6/1980 | Gerber | 433/197 |
| 4,533,325 A | | 8/1985 | Blair et al. | 433/171 |
| 4,650,417 A | * | 3/1987 | Schwartz | 433/196 |

FOREIGN PATENT DOCUMENTS

| | | | | |
|---|---|---|---|---|
| GB | 716895 | * | 10/1954 | 433/196 |
| JP | 50-155187 | | 12/1975 | |
| JP | 58-101621 | | 6/1983 | |
| JP | 58-101620 | | 7/1983 | |
| JP | 11-290347 | | 10/1999 | |

* cited by examiner

Primary Examiner—Cary E. O'Connor
(74) Attorney, Agent, or Firm—Perkins Coie, LLP

(57) ABSTRACT

Dentures are taught may comprise one or more false teeth that correspond to the upper and lower second premolars and/or first molars. The false tooth or teeth preferably have the following characteristics in relation to the upper and lower second premolars and first molars: (1) an imaginary plane passing through the supporting cuspals of the upper second premolars and the supporting cuspals of the upper first molars may be parallel or substantially parallel to the occlusal plane; (2) an imaginary plane passing through the base of the opposed-teeth contact region formed on the occlusal surface of the lower second premolars and the lower first molars may be parallel or substantially parallel to the occlusal plane; and (3) in centric occlusion, the supporting cusps of the upper second premolars and the supporting cusps of the upper first molars may contact the bases of the respective opposed-teeth contact regions formed on the occlusal surface of the lower second premolars and the lower first molars. Dentures are also taught that comprise a denture plate and a plurality of false teeth corresponding to lower first premolar, second premolar, first molar, and/or second molar, wherein the shapes of the opposed-tooth contact regions formed on the occlusal surfaces of the second premolar and the lower first molar have the following angular conditions:

(a) sagittal incisal guide angle$\geq$sagittal condylar guide angle and
(b) lateral incisal guide angle>sagittal condylar guide angle.

36 Claims, 10 Drawing Sheets

UPPER JAW  [7] [6] [5] [4] △ △ △ △ △ △ [4] [5] [6] [7]

LOWER JAW  △ 6 5 △ △ △ △ △ △ △ △ 5 6 △

△ : RESIN TOOTH 3

☐ : RESIN TOOTH 4

FALSE TEETH M : TEETH 1 WERE USED AS THE LOWER SECOND PREMOLAR AND FIRST MOLAR (LEFT AND RIGHT)
N : TEETH 2 WERE USED AS THE LOWER SECOND PREMOLAR AND FIRST MOLAR (LEFT AND RIGHT)
O : TEETH 3 WERE USED AS THE LOWER SECOND PREMOLAR AND FIRST MOLAR (LEFT AND RIGHT)
P : TEETH 4 WERE USED AS THE LOWER SECOND PREMOLAR AND FIRST MOLAR (LEFT AND RIGHT)

1 : CENTRAL INCISOR
2 : LATERAL INCISOR
3 : CANINE
4 : FIRST PREMOLAR
5 : SECOND PREMOLAR
6 : FIRST MOLAR
7 : SECOND MOLAR

FIG. 5

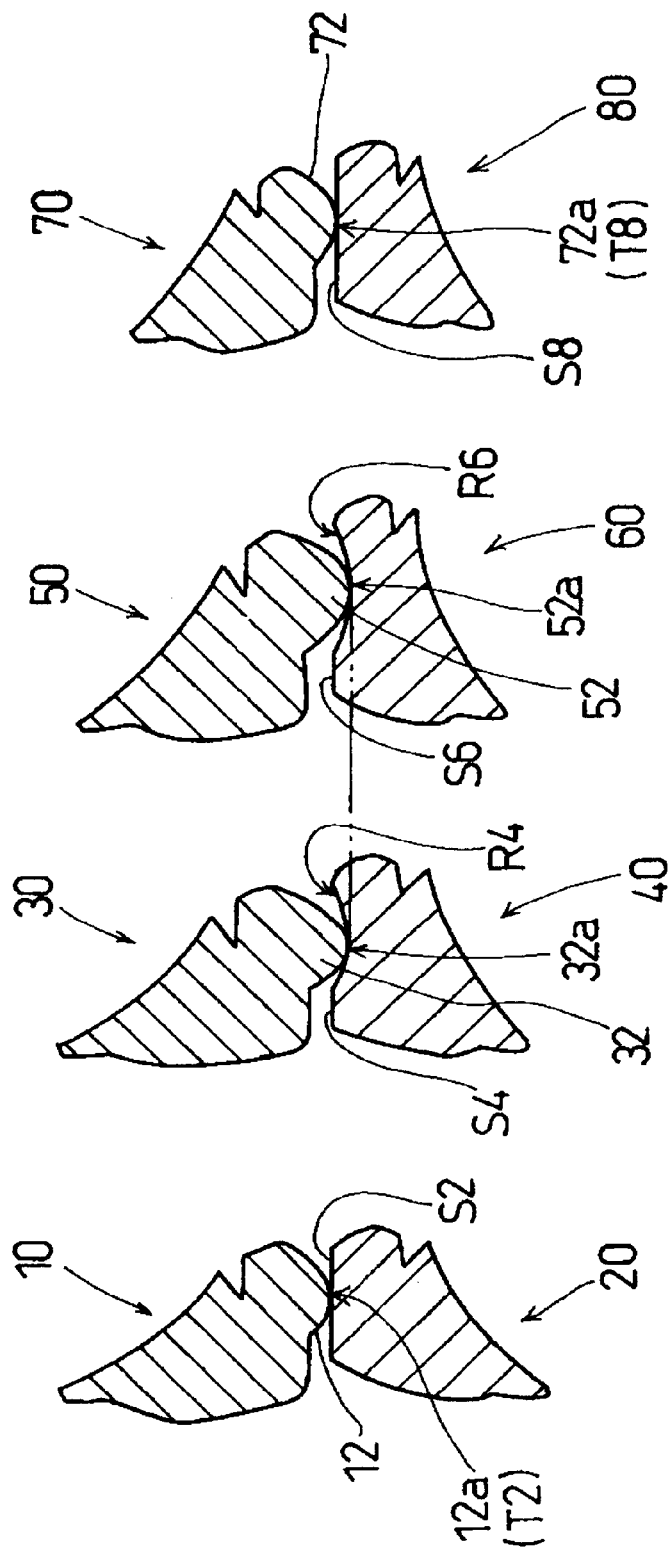

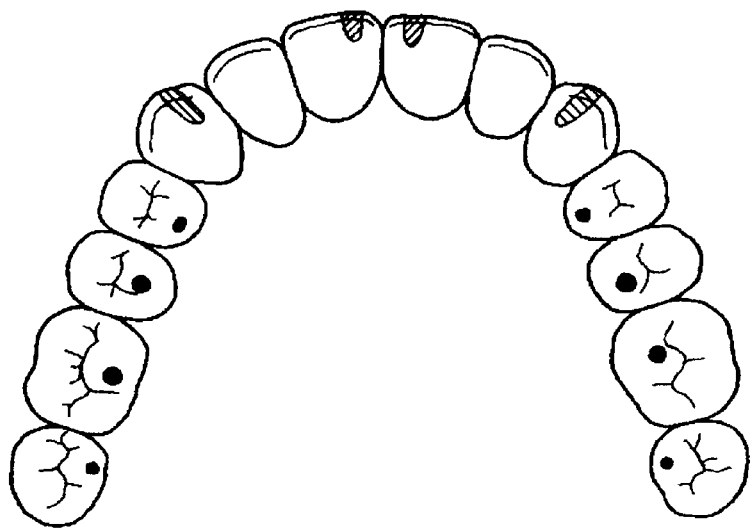
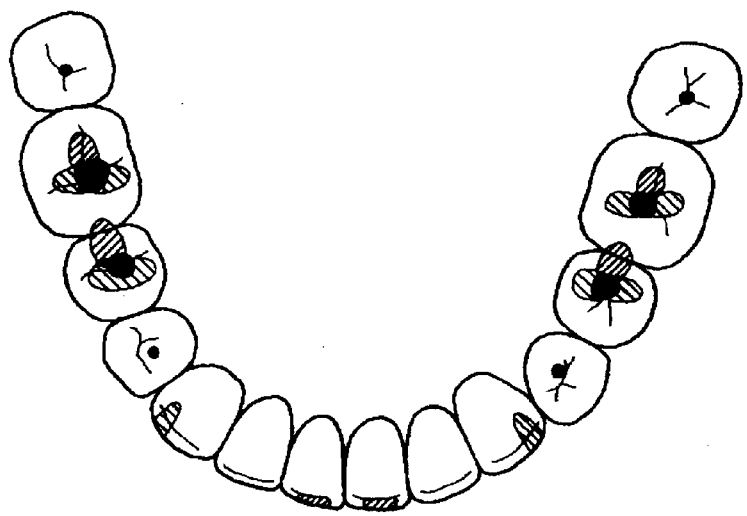
▨ : CONTACT REGION AT LATERAL MOVEMENT
▨ : CONTACT REGION AT FORWARD MOVEMENT
■ : CONTACT REGION AT CENTRIC OCCLUSION
FIG. 12

DENTURES AND FALSE TEETH

BACKGROUND OF THE INVENTION

1. Technical Field

The present invention relates to dentures and false teeth, which may preferably improve occlusion (i.e., the fitting together of the teeth of the lower jaw with the corresponding teeth of the upper jaw when the jaws are closed). The present invention also relates to methods for aligning dentures and false teeth. Further, the present invention relates to methods for treating and preventing maladies caused by malocclusion using the herein described dentures and false teeth.

2. Description of Related Art

Recent research has considered the relationship between malocclusion and geineralized symptoms (e.g., headaches, stiff shoulders, and back pain). There have already been reports of an improvement in various generalized symptoms through the correction of occlusion in patients fitted with full dentures or a splint in the oral cavity (see e.g., Nakamura, Shoji, "Factors of Occlusion-Related Diseases and Diagnosis and Treatment Thereof," P.J.A. Occlusion Health, Vol. 1 (1995)).

Known dentures are designed and produced so as to have the shape and function of natural human teeth because the dentures serve as a replacement for natural teeth. An examination of the shape of the occlusal surface of known false molars also reveals a shape that is designed and produced to be identical to the occlusal surface of natural molars (premolars and molars).

However, the configuration of dentures fitted with individual teeth identical in shape and function to natural teeth has been unable to provide preferred occlusion in patients requiring dentures. Even though the individual teeth satisfactorily perform the intended function, this alone is not adequate. Instead, dentures must provide appropriate occlusion in order to function satisfactorily.

Problems of the Prior Art Discovered by the Inventors

Previously, little thought was given to the balance in occlusal force (between, for example, adjacent molars and corresponding left/right molar pairs) during occlusion of the denture as a whole or at the center of occlusion. Therefore, wearing the denture worsened occlusion and produced various unpleasant conditions caused by malocclusion.

Development is therefore needed of not just individual false teeth, but also false teeth (molars) having a shape that considers the balance in occlusal force during occlusion (mastication) in order to prevent generalized symptoms associated with malocclusion. In addition, the development of a treatment that can prevent or cure malocclusion, and the associated generalized symptoms, also has been a long felt need.

When implanting a false tooth or denture, a dental technician or dentist must adjust the occlusal surface of the false teeth so as to appear natural in consideration of the dentition and occlusion of the recipient. Thus, the shape of the occlusal surface sometimes must be significantly modified by cutting. Moreover, after adjustment of the occlusal surface following implantation, the actual occlusion of the wearer will gradually change due to mastication and other various daily habits that affect occlusion.

If the occlusal surface is composed of a material that is hard or has a high wear resistance, cutting is problematic and the dental technician or dentist can not easily make initial occlusal adjustments. Further, such hard materials do not wear down in response to changes in the occlusion of the individual wearer, thereby creating a malocclusion. Moreover, improper occlusion is difficult to correct by cutting, due to the hardness of the occlusal surface.

SUMMARY OF THE INVENTION

It is, accordingly; one object of the present invention to provide improved false teeth and dentures.

Due to the perceived relationship between malocclusion and generalized symptoms apparently caused by malocclusion, the present teachings provide an occlusal configuration that readily maintains overall balance in occlusal force during occlusion. As a result, false teeth and dentures are described that are suitable for attaining preferred occlusion. Herein, preferred occlusion refers to a configuration for attaining opposed-tooth (or teeth) contact at the four points corresponding to the left and right upper second premolars and first molars. Preferably, the opposing teeth contact at four points from the lingual cuspals of the left and right upper second premolars to the proximal lingual cuspals of the upper first molars. Consequently, the present false teeth and dentures can prevent or substantially reduce the possibility of malocclusion and therefore, improve the satisfaction of the wearer.

In one aspect of the present teachings, dentures may have one or more false teeth selected from the upper and lower second premolars and first molars. The false tooth or teeth preferably have the following characteristics in relation to the upper and lower second premolars and first molars other than the false tooth or teeth named above:

(11) an imaginary plane passing through the supporting cuspals of the upper second premolars and the supporting cuspals of the upper first molars may be parallel or substantially parallel to the occlusal plane;

(2) an imaginary plane passing through the base of the opposed-teeth contact region formed on the occlusal surface of the lower second premolars and the lower first molars may be parallel or substantially parallel to the occlusal plane; and (3) in centric occlusion, the supporting cusps of the upper second premolars and the supporting cusps of the upper first molars may contact the bases of the respective opposed-teeth contact regions formed on the occlusal surface of the lower second premolars and the lower first molars.

If the above characteristics are utilized, the dentures may have the above-mentioned preferred occlusal configuration, which thereby provides balance during occlusion to the occlusal region extending from the upper and lower second premolars to the first molars. Further, the denture may maintain balance in occlusal force in all horizontal directions while the wearer is biting down and prevents occlusal force from becoming unbalanced in any horizontal direction. Thus, the occurrence of generalized symptoms connected to malocclusion are reduced or prevented. Such generalized symptoms discovered to result from improper occlusion include headaches, such as migraine headaches and stress-related headaches, stiff shoulders, lumbago, backaches, sore knees, shaking, numbing, and pain of the limbs, sore eyes, asthenopia, myodesopsia, tinnitus, hearing difficulties, insomnia, lethargy and hypertension.

Another aspect of the present teachings provides false teeth that may be utilized in the above-described dentures. Further, representative methods for making such dentures are taught that will provide the first through third occlusal configurations noted above.

In another aspect of the present teachings, representative methods for improving and treating occlusion-related conditions using one of the dentures of the invention are taught. In addition, methods for preventing occlusion-related conditions are taught using the present denture. More specifically, adjusting occlusion to bring about one of the above occlusal configurations using the present dentures improves or prevents conditions thought to arise in relation to occlusion (hereinafter referred to as occlusion-related conditions).

Another aspect of the present teachings provides a multi-layered false tooth that is formed from two or more layers in which the inside of the second or greater occlusal-surface-side layer has an internal layer that has a wear resistance and/or hardness greater than the wear resistance and/or hardness of the first occlusal-surface-side layer. As a result, wear of the false tooth is suppressed in the internal layer even when wear associated with mastication and other daily habits related to occlusion by the wearer of the false tooth has been caused in the first layer. Excessive wear of the occlusal surface and excessive occlusal variation are avoided by virtue of the internal layer. Such false teeth therefore provides satisfactory occlusion in individual wearers. Preferably, the false tooth adequately avoids wear as a result of such an internal layer.

Another aspect of the present teachings provides an implant comprising at least one false tooth of one of the above embodiments.

BRIEF DESCRIPTION OF THE DRAWINGS

FIG. 5 shows the positioning of the false teeth in the dentition of a full denture.

FIG. 9 buccolingually shows cross-sections that schematically illustrate occlusion of the opposing teeth in FIG. 6 of the invention.

FIG. 9(a) shows occlusion of the first premolars.

FIG. 9(b) shows occlusion of the upper and lower second premolars.

FIG. 9(c) shows occlusion of the first molars. FIG. 9(d) shows occlusion of the upper and lower second molars.

FIG. 10 buccolingually shows cross-sections that schematically illustrate occlusion during lateral movement (on the working side) of the opposing teeth in FIG. 6.

FIG. 11(a) shows occlusion of the upper and lower first premolars. FIG. 11(b) shows occlusion of the second premolars. FIG. 11(c) shows occlusion of the first molars. FIG. 11(d) shows occlusion of the second molars.

FIG. 12 is a view illustrating one example of preferred occlusion.

DETAILED DESCRIPTION OF THE INVENTION

Figure 1:
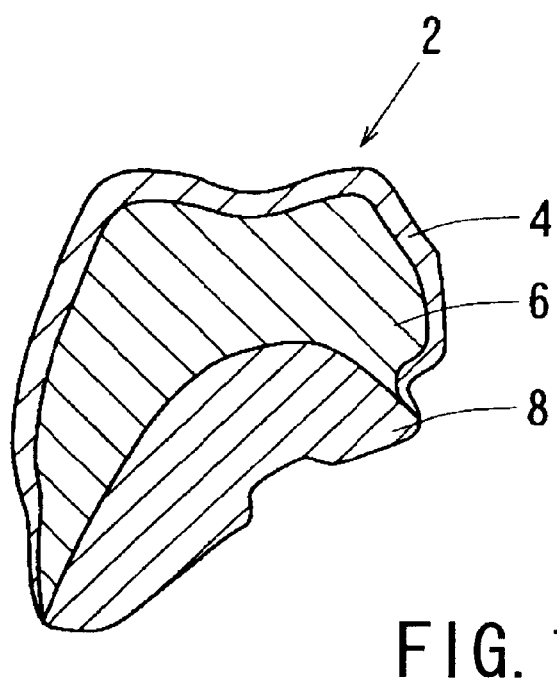
FIG. 1 shows cross-section view of a first representative false tooth.

Improved dentures, false teeth, methods for making such dentures and false teeth, and methods for preventing or treating symptoms caused by malocclusion are taught herein. Although not wishing to be bound by theory, these improvements are believed to generally relate to an occlusal configuration that allows opposed tooth contact at the four points corresponding to the left and right upper second premolars and first molars. For example, an ocelusal configuration is taught that allows opposed teeth to contact at four points from the lingual cuspals of the upper left and right second premolars to the linguoproximal cuspals of the upper first molars.

More preferably, the occlusal configuration does not prevent the upper first premolars and upper second premolars from contacting at the four points of the upper second premolars and the upper first molars. Specifically, in centric occlusion, the upper first premolars and second molars make opposed contact at points. (Opposed contact preferably occurs at a total of eight points.) The upper first premolars and second molars do not make opposed contact during lateral and forward movement.

By using one of the occlusal configurations of any of the present teachings, the severity of unpleasant symptoms linked to malocclusion in the patient can be prevented or substantially decreased. Furthermore, the application of such an occlusal configuration is believed to eliminate or decrease the severity of unpleasant symptoms of unknown causes.

Representative Dentures

The term "denture" refers to a dental plate having at least one false tooth attached to the dental plate. Preferably, dentures include at least one false tooth selected from the upper and lower second premolars and first molars. Dentures may more preferably comprise at least three false teeth selected from the upper and lower second premolars and first molar. Dentures may also comprise false teeth corresponding to three or more pairs of upper and lower teeth (for a total of six or more teeth). Most preferably, dentures may comprise false teeth corresponding to all said teeth (for a total of eight false teeth).

The false tooth or teeth disposed in the denture may preferably have at least the following characteristics in relation to the upper and lower second premolars and first molars other than the false tooth or teeth named above:

(1) on the upper-jaw side, the imaginary plane passing through the supporting cuspals of the upper second premolar and the supporting cuspals of the upper first molar is parallel or substantially parallel to the occlusal plane;

(2) on the lower-jaw side, the imaginary plane passing through the base of the opposed-tooth contact region formed on the occlusal surface of the lower second premolars and the lower first molars is parallel or substantially parallel to the occlusal plane; and (3) in centric occlusion, the supporting cusps of the upper second premolars and the supporting cusps of the upper first molars are in contact with the bases of the respective opposed-tooth contact regions formed on the occlusal surface of the lower second premolars and the lower first molars.

The term "occlusal surface" in the present specification, except where otherwise noted, refers to the area facing the opposing tooth surrounded by the cusps and edges (typically the anatomical occlusal surface). Moreover, the term "occlusal plane" in the specification, unless otherwise noted, refers to a plane passing through at least a portion of the molar occlusal surface positioned almost parallel to the imaginary occlusal plane in the intercuspal position (centric occlusion position), which has been decided by experts based on the Camper plane and the Frankfort plane.

When the imaginary plane passing through the vertex of the opposing-tooth contact region formed on the occlusal surface of the lower second premolars and lower first molars is formed almost parallel to the occlusal plane in the denture, selecting a stable occlusion position during mastication is simplified.

When the supporting cusps of the upper second premolars and the supporting cusps of the upper first molars are formed so as to make simultaneous contact in the opposed-tooth contact regions corresponding to the occlusal surfaces of the lower second premolars and the lower first molars, occlusion during mastication in the forward and lateral directions is readily stabilized.

If the false tooth is one or more of the lower second premolars and first molars, the shape of the opposed-tooth contact region formed on the occlusal surface of the false tooth or teeth preferably satisfies the following conditions:

(a) sagittal incisal guide angle≧sagittal condylar guide angle and (b) lateral incisal guide angle>sagittal condylar guide angle.

By utilizing these conditions, balance during occlusion in the occlusal region extending from the lower second premolar to the lower first molar is provided. Moreover, stable-occlusion during mastication is achieved.

If the denture has at least one false tooth corresponding to one or more of the lower second premolars and the lower first molars, the tooth contact regions formed on the occlusal surface of these lower molars are preferably smooth-surfaced. In such a denture, contact between the upper jaw-side molars (cusps) and the corresponding lower jaw-side molars (occlusal-surface contact region) is always stable during occlusion. Lateral movement during mastication is thus smooth, and an unbalance in occlusal force is prevented. The term "smooth-surfaced" herein describes a face having a smoothness adequate to prevent the cuspals of the upper molars from interlocking or latching during occlusion. The present false teeth may comprise grooves or troughs within a range in which the upper cuspals can smoothly occlude without interlocking.

If the present dentures have at least one false tooth corresponding to one or more of the upper and lower first premolars and/or second molars, one or both of the following characteristics also is preferably satisfied:

(a) the occlusal surface of the lower false teeth is almost parallel to the occlusal plane and/or (b) the imaginary plane passing through the cuspals of the upper false teeth is positioned almost parallel to the occlusal plane.

If the denture has such characteristics, the false tooth or teeth corresponding to the upper and lower first premolars and/or the second molars do not interfere with contact of the second premolars and the first molars during occlusion. Balanced occlusion of a higher order can thus be maintained. These characteristics contribute to a configuration in which the upper first premolar and the upper second molar do not prevent four-point opposed contact between the upper second premolars and the upper first molars.

In another preferred embodiment, the denture may comprise upper second premolars and first molars of an almost identical hardness, lower second premolars and first molars of an almost identical hardness, and lower second premolars and first molars with a hardness equal to or less than that of the upper second premolars and the first molars. The balance in the hardness of the upper and lower second premolars and the first molars of such a denture is excellent; therefore, satisfactory occlusion can be maintained for the long periods.

In order to maintain proper occlusal balance the hardness of at least the surface layer of the upper second premolars and the upper first molars—whether of a single-or multi-layer construction (the tooth typically has a two- or-three-layer construction)—should be nearly equal. The hardness of the lower second premolars and the lower first molars also should be equal or approximately equal. The hardness of the lower second premolars and the lower first molars should be equal to or less than the hardness of the upper second premolars and the upper first molars.

If the denture has upper and lower first premolars and/or second molars, the hardness of the surface layers thereof is preferably as follows:

(a) the surface layers between the upper first premolars and the second molars and those between the lower first premolars and the second molars should be equal or approximately equal;

(b) the hardness of the upper second premolars and the first molars should be equal, or approximately equal, to or greater than that of the upper first premolars and second molars;

(c) similarly, the hardness of the lower second premolars and first molars should be equal, or approximately equal, to or greater than the hardness of the lower first premolars and second molars. More preferably, the upper first premolars, second premolars, first molars, and second molars should all be of an identical hardness.

In centric occlusion, the denture preferably allows one-to-one opposed-tooth contact. More preferably, it allows one-to-one opposed-tooth contact during lateral and forward movement. The upper second premolars and first molars are preferably connected false teeth. The lower second premolars and first molars are also preferably connected false teeth.

The denture may also include a lower molar or molars having the following characteristics:

(a) the imaginary plane passing through the bases of the opposed-tooth contact regions formed on the occlusal surface of the lower second premolars and the lower first molars is parallel, or substantially parallel, to the occlusal plane and
(b) the imaginary plane passing through the vertexes of the opposed-tooth contact regions formed on the occlusal surface of the lower second premolars and the lower first molars is parallel, or substantially parallel, to the occlusal plane.

If the denture has a false tooth or teeth corresponding to one or more of the lower first premolars and the second molars, the base of the occlusal surfaces thereof may be made parallel to the occlusal plane. If the denture has false teeth corresponding to the lower first premolars, second premolars, first molars, and second molars, the denture may be made so that the bases of the occlusal surfaces of the first premolars and the second molars are parallel, or substantially parallel, to the occlusal plane and the bases of the occlusal surfaces of the second premolars. The first molars may be parallel, or substantially parallel, to the occlusal plane and located below the bases of the occlusal planes of the first premolars and the second molars.

The denture also may be formed with upper molars having the following characteristics:
(a) if the denture has false teeth corresponding to the upper first premolars, second premolars, first molars, and second molars, the supporting cuspals of the first premolars and the second molars are aligned, or substantially aligned, at an identical height in centric occlusion, and the supporting cuspals of the second premolars and first molars are aligned, or substantially aligned, at an identical height and located below the supporting cuspals of the first premolars and the second molars.
(b) the lines connecting the supporting cuspals of the first premolars to the second molars and the lines connecting the cuspals of the second premolars to the first molars may be positioned parallel, or substantially parallel, to the occlusal plane.

Representative False Teeth

Preferably, the false tooth or teeth correspond(s) to the lower second premolars or the lower first molars. The shape of the opposed-tooth contact region formed on the occlusal surface thereof preferably satisfies the following conditions:
(a) sagittal incisal guide angle$\geq$sagittal condylar guide angle and
(b) lateral incisal guide angle>sagittal condylar guide angle.

More preferably, the occlusal surface is smooth-surfaced and the lower second premolars and the lower first molars are preferably connected. Preferably, a set of a false tooth are utilized and may include false teeth corresponding to the lower first premolar, second premolar, first molar, and second molar. The shapes of the opposed-tooth contact regions formed on the occlusal surfaces of the second premolar and the first molar may further satisfy the following angular conditions:
(a) sagittal incisal guide angle$\geq$sagittal condylar guide angle and
(b) lateral incisal guide angle>sagittal condylar guide angle.

Moreover, the shapes of the opposed-tooth contact regions on the occlusal surfaces of the first premolar and the second molar may satisfy the following conditions:

(a) sagittal incisal guide angle$\geq$sagittal condylar guide angle and
(b) lateral incisal guide angle>sagittal condylar guide angle or the shapes are sloped more gently than a shape satisfying the above angular conditions. Preferably, the false teeth corresponding to the upper second premolars and the upper first molars comprise lingual cuspals as the only portion of opposed contact, the lingual cuspals are partial spheres, and the false teeth are connected.

A variety of internal shapes and false tooth materials may be used for the false teeth of the denture. For example, the boundary layer of the layers of a false tooth may have a two- or three-layer construction (i.e., a two-layer construction with surface and base layers or a three-layer construction with surface, intermediate, and base layers) comprising resins, metals, or ceramics of differing properties and may be made parallel, or substantially parallel, to the occlusal plane P.

If, for example, the portion forming the vertexes of the occlusal surfaces of the lower molars (the second premolars and the first molars in particular) have a two- or three-layer construction, the boundary layer of the intermediate or base layer thereof would preferably be formed so as to be almost parallel to the occlusal plane P in centric occlusion when viewed buccolingually in cross-section. With such a configuration, the difference between the quality, quantity, hardness, density, and other properties in the layers comprising the false tooth made of resin, metal, or a ceramic does not affect occlusal balance and thus allows a more precise occlusal balance to be maintained. This effect is particularly pronounced in the lower second premolars and first molars.

For multi-layered false teeth, making the hardness and/or wear resistance of the surface layer of the upper and lower second premolars and first molars (particularly that or those of the lower second premolars and first molars) greater than the hardness and/or the wear resistance of the other false molar or molars is preferable in order to maintain long-term occlusal balance.

If the false tooth has a multi-layered construction, the false tooth preferably has at least two layers, consisting of at least one layer that includes the occlusal surface and a more inward layer, meaning a lower layer toward the root side. Generally, such multi-layer false teeth are formed by layering a synthetic resin. Such a false tooth is well suited to provide preferred occlusion.

Figure 2:
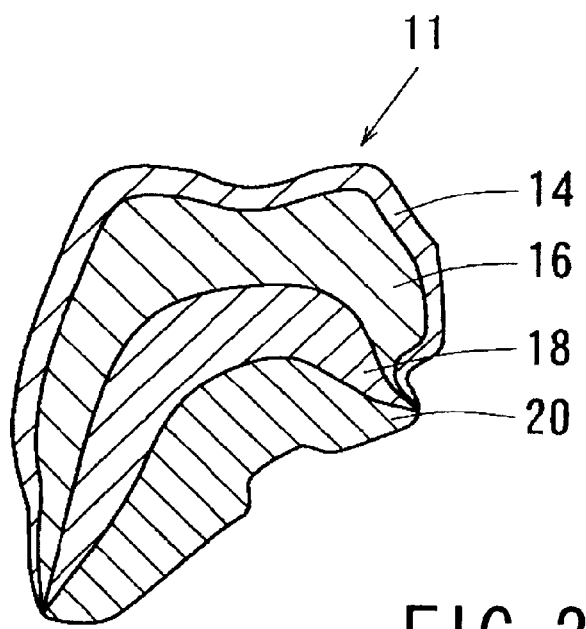
FIG. 2 shows cross-section view of a second representative false tooth.

FIG. 1 shows a cross section of a representative false tooth 2 having a three-layer construction of three layers 4, 6 and 8. FIG. 2 shows a cross section of a representative false tooth 11 having a four-layer construction of four layers 14, 16, 18, and 20. The bottommost layers 8 and 20 of the false teeth 2 and 11 both function as adhesion layers. In the alternative, the false tooth may be adhered to the dental plate using an adhesive instead of such an adhesive layer.

One of the internal layers further inward than the first layer that includes the occlusal surface has a greater wear resistance and/or a hardness. This internal layer may be formed as the second layer or the third layer. It should be formed farther inward than the first layer. Preferably, it is formed as the second layer. The Vickers hardness of the first layer, which includes the occlusal surface, may be preferably between about 15 and 60. If the first layer has a hardness in this range, the occlusal surface wears in a manner appropriate to the occlusion of the individual wearer, the inside layer suppresses excessive wear, and satisfactory occlusion is maintained. The upper limit for the hardness is about 30, more preferably is about 25 and most preferably is about 20.

No particular measurement of hardness is required, but JIS (Japanese Industrial Standard) Z2244 is preferable. Moreover, it is preferable to use the Vickers hardness measured with this testing method as a standard. When Vickers hardness is measured according to JIS Z2244, the testing conditions should be a load of 1 kg for 15 seconds. In addition, no particular measurement of wear resistance is required, but JIS K7204 is preferable. Moreover, it is preferable to use the amount of wear determined with the testing method as a standard.

An amount of wear of 10 mg or less as determined by the wear-resistance test of JISK7204 is preferable for the first layer. If the amount of wear is in this range, the occltisal surface wears appropriately when the wearer masticates while wearing the false tooth. At a value greater than 10 mg, grinding and wear readily occur. Excessive wear naturally does not pen-nit appropriate occlusion. A more preferable value is about 5 mg or less. The testing conditions in the wear-resistance testing are preferably 300 rotations at 60 rpm and 23° C. using a CS17 grinding wheel.

Thus, the first layer of the false tooth preferably has a Vickers hardness value in a range from about 15 to 60 and an amount of wear of about 10 mg or less. The first layer more preferably has a Vickers hardness value of about 30 or less and even more preferably of about 25 or less and the amount of wear is about 10 mg or less and more preferably about 5 mg or less.

No particular limitations are placed on the materials that compose the first layer, as long as the preferred wear resistance and/or hardness is achieved. For example, the main ingredient is preferably a (meth)acrylic resin, such as a polyalkyl (meth)acrylate. The alkyl group preferably has from one to four carbon atoms. (Meth)acrylate monomers with differing numbers of carbon atoms are preferably used in a copolymer. Polymethyl (meth)acrylate is preferably the main ingredient. A cross-linking agent may be added to the materials to adjust the degree of cross-linking. An inorganic compound or other filler may be added to adjust the wear resistance and/or hardness. Silica or a similar material is preferably used as the filler. Such a first layer allows satisfactory occlusal wear by the wearer to provide preferred occlusion in the individual user, improves resistance to staining, and suppresses discoloration and the adherence of plaque. Moreover, satisfactory cutting power is provided, and occlusal adjustment by a dentist or dental technician is greatly simplified.

Preferably, the wear resistance and/or hardness of the internal layer is greater than the wear resistance and/or hardness of the first layer and preferably prevents excessive wear during occlusion by the individual wearer. The Vickers hardness value of the internal layer is preferably in a range from about 25 to 200. A value in this range effectively suppresses wear. At a value below 25, wear hampers stable occlusion, and at a value above 200, the false tooth becomes brittle. A more preferable range is from about 30 to 150. A hardness of 70 or above prevents wear from mastication. In other words, the Vickers hardness of the internal layer is preferably at least 10 greater than the Vickers hardness value of the first layer and is equal to or less than 200.

The amount of wear in the internal layer as determined by JIS K7204 is preferably in a range from about 0.1 mg to 3 mg. Wear is effectively suppressed in this range. At a value below 0.1 mg, the tooth becomes brittle, and above 3 mg, wear hampers stable occlusion. A more preferable range is from about 0.5 mg to 2 mg.

No particular limitations are placed on the materials that compose the second layer, as long as the preferred wear resistance and/or hardness is achieved. For example, a urethane resin such as a urethane-dimethacrylate copolymer is preferable. A cross-linking agent may be added to the material to adjust the degree of cross-linking. An inorganic or other filler may be added to adjust the wear resistance and/or hardness. Silica or a similar material is preferably used as the filler.

If such an internal layer is provided, the false tooth suppresses wear in the internal layer even when wear has occurred in the first layer. Thus, excessive wear to the occlusal surface and variation in occlusion can be avoided and the occlusion of the individual wearer is maintained. Such an internal layer allows for a false tooth of adequate hardness and improves stability during occlusion.

Figure 3:
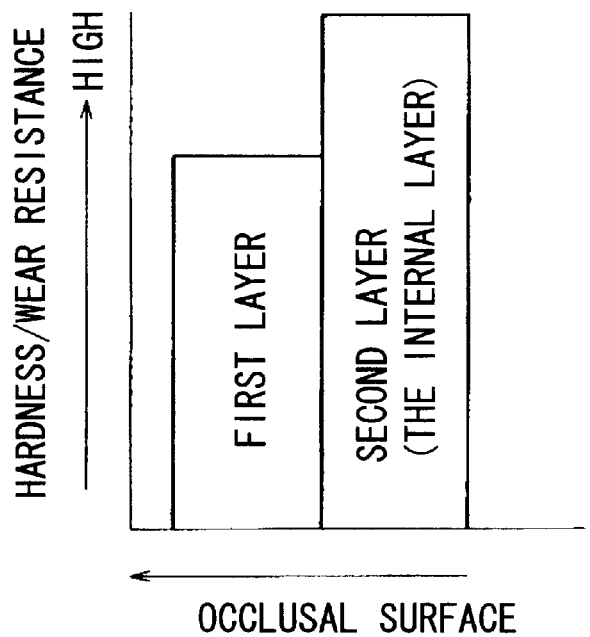
FIG. 3 shows differences in wear resistance. and/or hardness of the layers in the first representative false tooth.

FIG. 3 illustrates the relationship between the wear resistance and/or the hardness of the first layer and the internal layer when the internal layer is formed in the second layer of the false tooth. In this embodiment, a third or greater layer with a wear resistance and/or hardness greater than the wear resistance and/or hardness of the second layer may be provided in the false tooth. The third or greater. layer may also have a wear resistance and/or hardness less than the wear resistance and/or hardness of the second layer.

Figure 4:
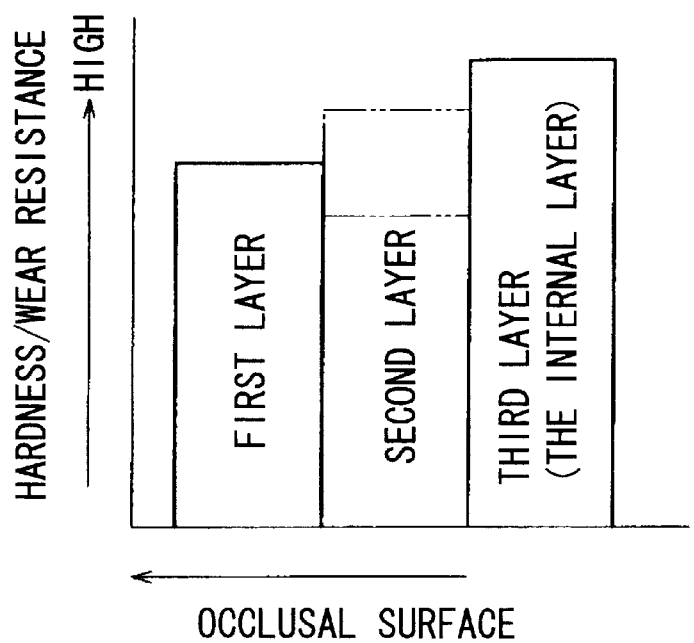
FIG. 4 shows differences in wear resistance and/or hardness of the layers in the second representative false tooth.

FIG. 4 shows two embodiments and illustrates the relationship between wear resistance and/or hardness in the first layer, second layer, and third layer when the internal layer is formed on the third layer. The wear resistance and/or hardness of the second layer may be greater or less than that or those of the first layer. In these embodiments, a fourth or greater layer of a wear resistance and/or hardness greater than that or those of the third layer may be provided in the false tooth. The fourth or greater layer may also have a wear resistance and/or hardness less than that or those of the third layer.

A denture having such a false tooth may be made by attaching the false tooth to a dental plate, thereby providing preferred occlusion in its individual wearers. If a full denture is prepared, the present false teeth may be used as one or all the false teeth. More preferably, the denture comprises the above-described false tooth. as at least one of the upper and lower first and second premolars and first and second molars. The present false teeth are preferably utilized as at least one of the upper and lower second premolars and first molars, because these teeth heavily influence the center of occlusion. The false tooth is more preferably utilized as one or both of the lower second premolars and the first molars.

Representative Implant

Implants comprising one or more of the above false tooth are also taught. The implant may correspond to the range of teeth from the upper and lower first premolars to the second molars. An implant having false tooth of the above-described multi-layer construction may also be prepared. Such an implant allows for satisfactory occlusion in its individual wearers while strongly resisting staining and simplifying occlusal adjustment.

Representative Examples

Further representative examples of the present teachings will now be described in further detail with reference to the attached drawings. This detailed description is merely intended to teach a person of skill in the art further details for practicing preferred aspects of the present teachings and is not intended to limit the scope of the invention. Only the claims define the scope of the claimed invention. Therefore, combinations of features and aspects disclosed in the following detail description may not be necessary to practice the invention in the broadest sense, and are instead taught merely to particularly describe some representative examples of the invention. Moreover, various features of the representative examples may be combined in ways that are not specifically enumerated in order to provide additional useful embodiments of the present teachings.

All descriptions and figures of the denture of this embodiment regard the left buccal side, but similar molars may be symmetrically provided on the right buccal side.

Figure 6:
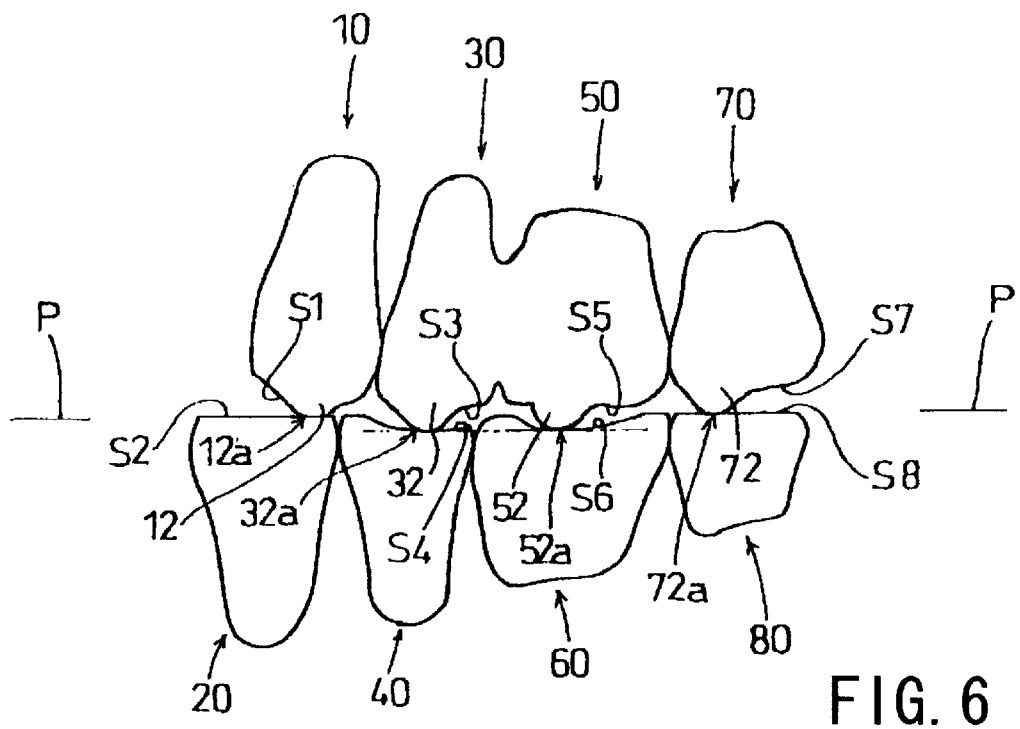
FIG. 6 is a schematic buccal view depicting the left buccal false molars in the representative denture in centric occlusion shown as a cross section along the line connecting the, upper supporting cuspals of the molars.
Figure 8:
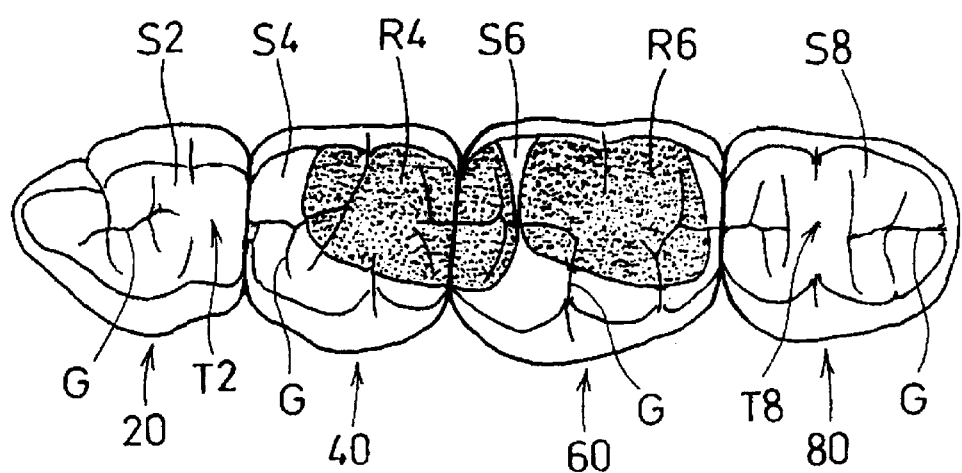
FIG. 8 is a schematic dentition view depicting the occlusal surfaces of the left lower false molars of the representative denture.

As is shown in FIGS. 6 and 8, the general external appearance of molars 10, 20, 30, 40, 50, 60, 70, and 80 of the denture in this embodiment resemble the appearance of a natural molar, as is the case with known dentures. The molars are typically formed of a ceramic, metal, or plastic (resin). As is the case with known false molars, the molars are arranged and affixed via an appropriate dental-plate material or directly at set locations within the oral cavity. Preferred shapes and arrangements of the lower molars 20, 40, 60, and 80 will be described first.

As is shown in FIGS. 6 and 9, the occlusal surface S of the lower first premolar 20 and the second molar 80 is flat as a whole, lacking the bumps prominent when these teeth are viewed laterally. The occlusal surface S may take a shape approximating that of the tooth contact region of the occlusal surface of the lower second premolar 40 and the first molar 60 or may be plate-shaped and slope more gently. The surface has a smoothness that prevents the cuspals of the opposing upper molars from interlocking or latching with the lower molars, which means that it is smooth-surfaced. Occlusal surfaces S2 and S8 may comprise grooves or troughs within a range in which the upper cuspals can smoothly occlude without interlocking with the lower cuspals.

As can be seen, the flat occlusal surfaces S2 and S8 are formed and arranged so as to include the imaginary plane that runs nearly parallel to the occlusal plane P. (Here, the two nearly overlap.)

As is shown in FIGS. 6 and 8, the lower second premolar 40 and the first molar 60 of this embodiment are prepared individually. Occlusal surfaces S4 and S6 of the molars 40 and, 60 differ from those of molar 110 in that tooth contact regions R4 and R6 (FIG. 8)—in which supporting cusps 32 and 52 of the opposed upper second premolar 30 and the first molar 50 can come into contact during mastication—have a concave configuration. FIGS. 6 and 9 show that contact regions R4 and R6 comprise shallow troughs lacking bumps formed so that shallow, mortar-like curved surfaces appear in the cross section thereof. These curved surfaces are also smooth-surfaced.

In centric occlusion, the bases of the contact regions R4 and R6 of the molars 40 and 60 (i.e., the bases of the occlusal surfaces S4 and S6) are formed and arranged almost parallel to the occlusal plane P. The plane that contains these bases is located below the plane that contains the occlusal surfaces S2 and S8. Further, in centric occlusion, the vertexes of the contact regions R4 and R6 of the molars 40 and 60 (which are shown here on the distal edges of the contact regions R4 and R6) are formed and arranged so as to be almost parallel to the occlusal plane P.

The lower jaw is thus located in the position closest to the upper-jaw-side (i.e., upward position) in centric occlusion for the denture of this embodiment. Therefore, the position of the lower jaw during forward and lateral lower-jaw movement during mastication is more distant from the upper jaw (i.e., downward position) than it is in centric occlusion.

The lower second premolar 40 and the first molar 60 may be connected as one in the form of a joined tooth. When the upper second premolar and first molar are a connected tooth, the lower second premolar 40 and the first molar 60 are preferably formed individually.

The diameters and the shapes (gradient) of the bowl-shaped curved surfaces of the contact regions R4 and R6 are formed in consideration of forward and lateral movement of the lower jaw during mastication. The curved surfaces of the contact regions R4 and R6 are shaped so that supporting cusps 32 and 52 formed on opposed molars 30 and 50 of the upper jaw, which will be discussed below, follow and touch the curved mortar-shaped face of the contact regions R4 and R6 in forward and lateral movement of the lower jaw during mastication. While there are no particular limits to the above constructions, the curved surface is preferably shaped to satisfy the following conditions when the false tooth is made with a so-called adjustable articulator (not shown):

(i) sagittal incisal guide angle$\geq$sacittal condylar guide angle and (ii) lateral incisal guide angle>sagittal condylar guide angle.

The shape of the curved surface is decided and embodied with the conditions set as above. In this case, it is preferable that:

lateral condylar guide angle=sagittal condylar guide angle/8+12.

As is shown in FIG. 8, occlusal surfaces S2, S4, S6 and S8 corresponding to the upper surfaces of the lower molars 20, 40, 60, and 80 have grooves G in all locations, as is the case in natural teeth, so that masticated items are easily ejected from the occlusal surface during mastication. As shown in FIG. 8, the portions and vicinity thereof (portions T2 and T8 in the figure) in which the occlusal surfaces S2 and S8 of the lower first premolar 20 and second molar 80 make contact with the opposed molars (i.e., the upper first premolar 10 and second molar 70) are preferably smooth-surfaced.

Upper molars 10, 30, 50, and 70 will be discussed next. These upper molars correspond (oppose) the above-mentioned lower molars 20, 40, 60, and 80. As is seen in FIGS. 6 and 9, one supporting cusps 12, 32, 52, and 72 is formed in each of the upper molars 10, 30, 50, and 70. In greater detail, one lingual supporting cusp is formed on the lingual side of the molars 10, 30, 50, and 70, as is seen if FIG. 9. The supporting cusps 52 and 72 of the upper first molar 50 and the second molar 70 are both formed proximally (FIG. 6). A buccal cusp is located on each of the upper molars 10, 30, 50, and 70, but is formed so as not to make substantial occlusive contact.

The molars are aligned on the upper-jaw side so that lines connecting the points of the supporting cusps 12, 32, 52, and 72 (i.e., supporting cuspals 12a, 32a, 52a, and 72a) are almost straight when viewed from the occlusal surface. The supporting cuspals 12a, 32a, 52a, and 72a are shaped as bumps with a curved face lacking corners to resemble the tip of a wooden pestle or, in other words, as partial spheres.

Figure 13:
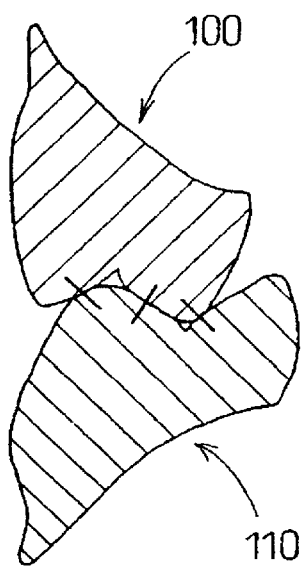
FIG. 13 buccolingually shows a cross-section that schematically illustrates the centric occlusion of the false molars of the known art as viewed from the distal direction (behind).
Figure 14:
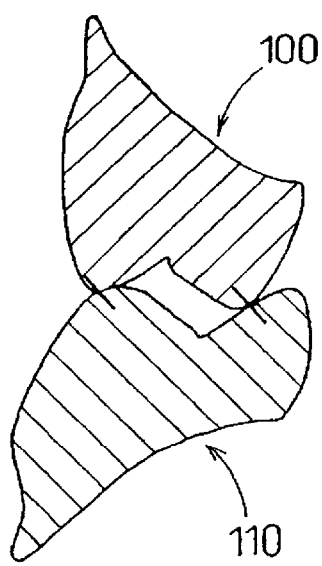
FIG. 14 buccolingually shows a cross-section that schematically illustrates the occlusion of the false molars of the known art during mastication.

Other supporting cusps or guiding cusps are not formed on any of the upper molars 10, 30, 50, and 70. Thus, unlike the case with known false teeth 100 and 110 (FIGS. 13 and 14), only supporting cusps 12, 32, 52, and 72 come into contact with the opposing occlusal surfaces S2, S4, S6, and S8 of the lower molars during occlusion (mastication) to shred and grind food and other items.

The supporting cuspals 12a and 72a of the upper molars 10 and 70 are arranged at a nearly identical height. The supporting cuspals 32a and 52a of the upper molars 30 and 50 are also arranged at a nearly identical height and are positioned lower than the supporting cuspals 12a and 72a. The plane passing through the supporting cuspals 12a and 72a and the plane passing through the supporting cuspals 32a and 52a are parallel, with the latter located in a lower position.

As shown in FIGS. 6 and 9, the supporting cusps 32 and 52 (i.e., the supporting cuspals 32a and 52a) of the upper second premolar 30 and first molar 50 are shaped so as to match with the contact regions R4 and R6 on the occlusal surfaces S4 and S6 of the lower second preimnolar 40 and first molar 60 that correspond to (oppose) the former in centric occlusion. At the time of contact, the imaginary plane passing through the supporting cuspals 32a and 52a (see the double-dot dot-dash line in the figures) is almost parallel to the occlusal plane P and is located in a fixed position within the oral cavity.

On the other hand, the supporting cusps 12 and 72 of the upper first premolar 10 and second molar 70 are shaped so as to make slight contact with contact portions T2 and T8 of the occlusal surfaces S2 and S8 formed in the corresponding (opposing) lower first premolar 20 and the second molar 80 in centric occlusion. At the time of contact, the imaginary plane passing through the supporting cuspals 12a and 72a (see the double-dot dot-dash line in the figures) is almost parallel to the occlusal plane P and is located in a fixed position within the oral cavity. In this manner, the supporting cusps 12, 32, 52, and 72 of the upper molars 10, 30, 50, and 70 are formed on the left buccal side shown and the right buccal side is not shown in the figures.

Occlusion provided by the denture of this embodiment formed in the above manner will be described next. First, one-to-one tooth contact at eight points is maintained between the upper supporting cuspals 12a, 32a, 52a, and 72a with bump-shaped curved faces and the occlusal surfaces (i.e., the contact portions T2 and T8 and the contact regions R4 and R6 of the lower molars 20, 40, 60, and 80 opposed thereto) in centric occlusion.

As would be expected, the supporting cusp 32 of the upper premolar 30 and the supporting cusp 52 of the first molar 50, which are almost parallel to the occlusal plane P, make contact respectively with the bases of contact region R4 on the occausal surface S4 of the lower second premolar 40 and the base of the contact region R6 on the occlusal surface S6 of the first molar 60, which are almost parallel to the occlusal plane P. As a result, occlusal balance is achieved due to these two molar pairs (i.e., the second premolars 30 and 40 and the first molars 50 and 60). In other words, occlusal contact is provided at four points on the left and right, because the occlusal force (pressure) generated in this configuration is applied equally to the two pairs of molars 30, 40, 50, and 60 while left/right balance is kept almost perpendicular to the occlusal plane P. Thus, the remaining two molar pairs (i.e., the first premolars 10 and 20 and the second molars 70 and 80), as was described above, come into contact only at contact portions T2 and T8 so as not to disrupt occlusal balance.

Figure 7:
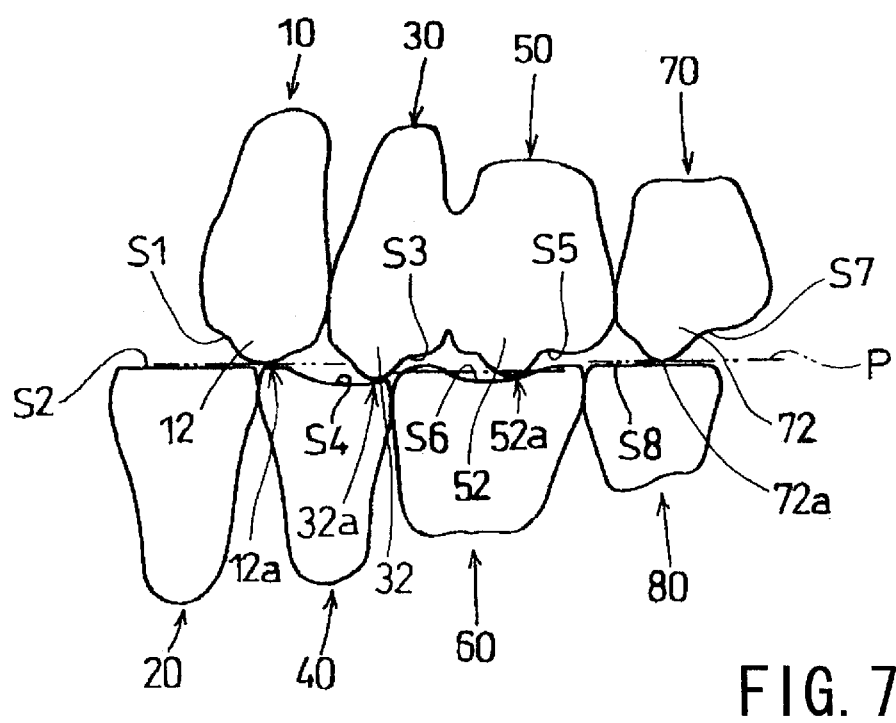
FIG. 7 is a schematic buccal view depicting the left buccal false molars of the representative denture during forward movement shown as a cross section along the line connecting the upper supporting cuspals of the molars.

Forward and lateral movement of the denture in this embodiment during mastication will be described next. First, forward movement will be described. During forward movement of the lower jaw in mastication as shown in FIG. 7, the supporting cusps 32 and 52 (i.e., the cuspals 32a and 52a) of the upper second premolar 30 and first molar 50 make simultaneous contact respectively with the vertexes (which correspond to the distal edges) of the occlusal contact regions R4 and R6 of the opposing lower-jaw second premolar 40 and first Molar 60. As FIGS. 6 and 7 show, the supporting cusps 32 and 52 (i.e., the cuspals 32a and 52a) make simultaneous contact with contact regions R4 and R6 so as to remain parallel to the occlusal plane P during forward movement of the lower jaw due to the curved surfaces of the contact regions R4 and R6.

On the other hand, the supporting cusps 12 and 72 (i.e., the cuspals 12a and 72a) of the upper first premolar 10 and the second molar 70 do not make contact with the flat occlusal surfaces S2 and S8 of the opposing lower first premolar 20 and the second molar 80. As FIG. 7 illustrates, the provision of curved surfaces in the contact regions R4 and R6 results in the supporting cuspals 12a and 72a not being able to make contact with the contact portions T2 and T8 during forward movement, in which the position of the lower jaw is below the centric occlusion position. (In other words, the contact portions T2 and T8 only make contact with the opposing supporting cuspals of the molars in centric occlusion.)

A balance in occlusal force is maintained during forward movement due to the intermolar movement described above. As a result of the upper and lower first premolars 10 and 20 and the second molars 70 and 80 not coming into contact, occlusal force acts on the upper second premolar 30 and the first molar 50 and the lower second premolar 40 and/or the first molar 60 with which these upper molars make contact. In this embodiment, the upper and lower second premolars 30 and 40 and the upper and lower first molars 50 and 60 touch on a tooth-to-tooth basis. When this happens, the supporting cusps 32 and 52 of the upper second premolar 30 and the molar 50 are almost parallel to the occlusal plane P and simultaneously make contact with the corresponding contact regions R4 and R6, as was described above. As a result, occlusal force (pressure) almost perpendicular to the occlusal plane P acts on these molars to maintain occlusal balance.

Movement during lateral movement will be explained next. During lateral movement of the lower jaw in conjunction with mastication shown in FIGS. 10 and 11, the supporting cusps 32 and 52 (i.e., the cuspals 32a and 52a) of the upper second premolar 30 and the first molar 50 respectively make simultaneous contact with the vertexes of the occlusal surface contact regions R4 and R6 (which correspond to the lingual-side edge on the working side and the buccal edge on the balancing side) of the opposing lower second premolar 40 and the first molar 60. Because the contact regions R4 and R6 have curved surfaces as described above, the supporting cusps 32 and 52 (i.e., the cuspals 32a and 52a) make simultaneous contact with contact regions R4 and R6 so as to remain parallel to the occlusal plane P during lateral movement of the lower jaw (from the working side to the supporting side), as is the case during forward movement.

Figures 10A, 10B, 10C, 10D:
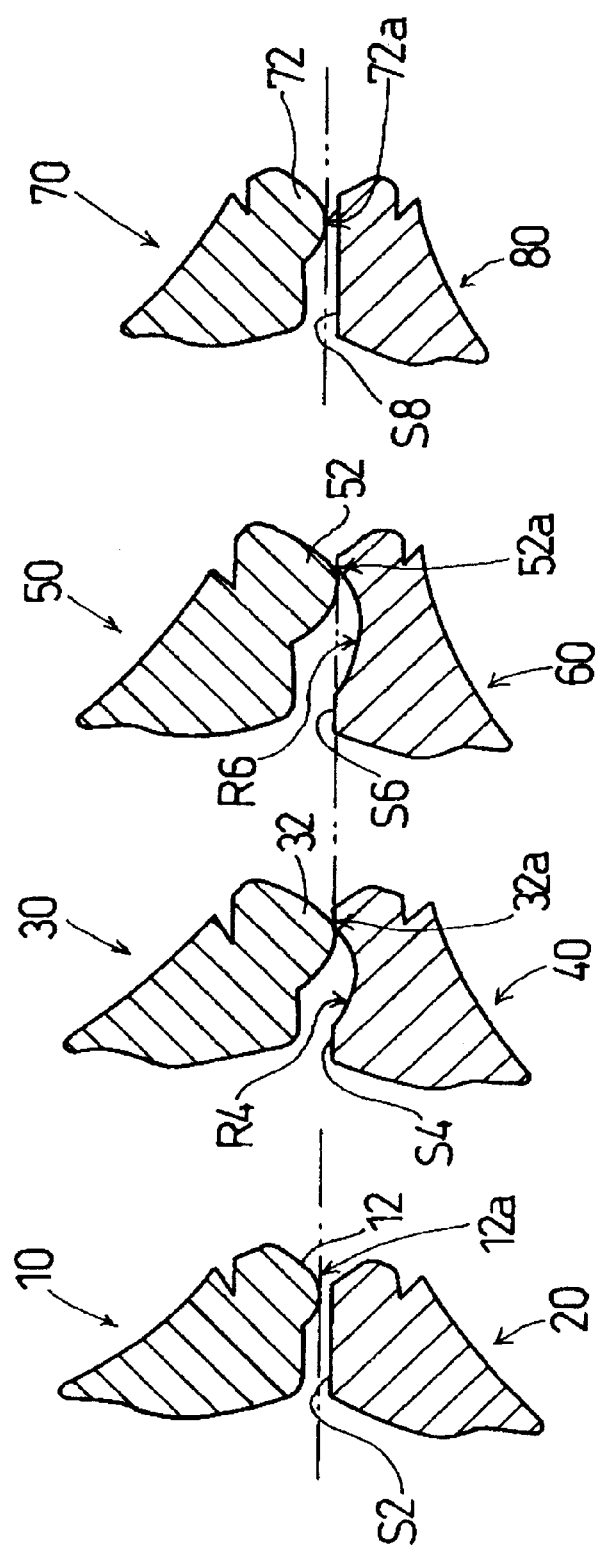
FIG. 10(a) shows occlusion of the upper and lower first premolars.
FIG. 10(b) shows occlusion of the second premolars.
FIG. 10(c) shows occlusion of the first molars.
FIG. 10(d) shows occlusion of the second molars.
Figure 11:
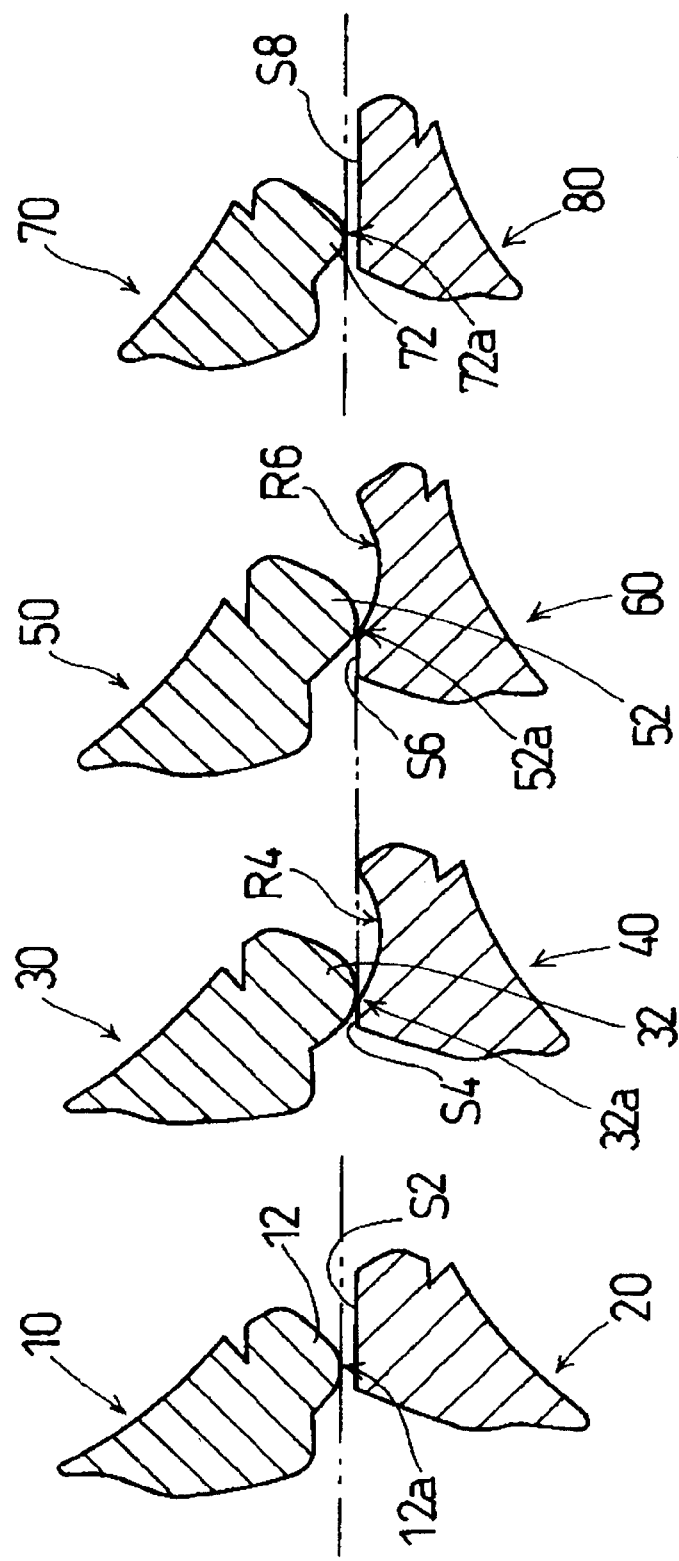
FIG. 11 buccolingually shows cross-sections that schematically illustrate occlusion during lateral movement (on the balancing side) of the opposing teeth in FIG. 6.

On the other hand, the supporting cusps 12 and 72 (i.e., the cuspals 12a and 72a) of the upper first premolar 10 and the second molar 70 do not make contact with the flat occlusal surfaces S2 and S8 of the opposing lower first premolar 20 and the second molar 80. As FIGS. 10, 11(a), and 11(d) illustrate, the provision of curved surfaces in the contact regions R4 and R6 results in the supporting cuspals 12a and 72a not being able to make contact with the contact portions T2 and T8 during lateral movement in which the position of the lower jaw is below the centric occlusion position.

A balance in occlusal force is maintained during lateral movement due to the intermolar movement described above. As a result of the upper and lower first premolars 10 and 20 and the second molars 70 and 80 not coming into contact, occlusal force (pressure) acts on the upper second premolars 30 and 40 and the first molars 50 and 60. When this happens, the supporting cusps 32 and 52 of the upper second premolar 30 and the molar 50 are almost parallel to the occlusal plane P and simultaneously make contact with the corresponding contact regions R4 and R6, as was described above. As a result, occlusal force almost perpendicular to the occlusal plane P acts on these molars to maintain occlusal balance.

Thus, the denture of this embodiment maintains occlusal balance in centric occlusion and during forward and lateral movement accompanying mastication. Therefore, unbalanced intertooth contact during biting down and mastication is eliminated to allow congruous and stable occlusion. Such occlusion prevents or ameliorates generalized conditions linked to malocclusion.

While preferred embodiments of the invention have been described, the present denture may be any item formed so as to have the above characteristics and is not limited to the embodiments illustrated above. In the above embodiments, the upper and lower first prermolars 10 and 20 and the second molars 70 and 80 make contact with the contact portions T2 and T8 in centric occlusion, but the invention is not limited thereto. For example, no contact is required. Even with such a construction, opposed contact in the occlusal region of the upper and lower second premolars 30 and 40 and the first molars 50 and 60 would maintain overall occlusal balance, as is the case in the above embodiment.

Although the above embodiment describes a denture having all the molars, the second molar, for example, could be omitted for a patient with small jaws. Another example is a denture with remaining natural or existing first premolars and second molars. In the case of such a denture, an adjustment would have to be made so that the first premolars and second molars would or would not make contact in centric occlusion in order to avoid disrupting occlusal balance between the false teeth corresponding to the second premolars and the false teeth corresponding to the first molars.

A description will now be provided of cases in which generalized symptoms steimniing from malocclusion were ameliorated using the denture and false teeth of the present teachings.

Case 1

Patient: A 72-year-old female.

Symptoms: Headache, shoulder pain, stiff shoulders, knee pain, and tinnitus.

False teeth:

Upper jaw: All left and right teeth (14)

Lower jaw: All teeth except for the right canine (13)

Of these, the 16 false teeth corresponding to the upper and lower first premolars, second premolars, first molars, and second molars were the false teeth described in the above embodiments and shown in FIGS. 6–11. The others were known false teeth. The non-false tooth of the patient (the lower right canine) was her remaining natural tooth.

Preparation of Denture

The denture was prepared using the above-mentioned false teeth. Further the denture was prepared in conjunction with an articulator so that in centric occlusion, the supporting cusps (supporting cuspals) of the upper second premolars and first molars would properly make contact with the base of the contact region on the occlusal surface of the lower second premolars and first molars. Further, the supporting cusps of the upper first premolars and second molars would make slight contact with the occlusal surface formed on the lower first premolars and second molars. The denture was similarly further prepared using an articulator so that during frontal movement of the lower jaw, the supporting cusps (supporting cuspals) of the upper second premolars and the first molars would make simultaneous contact respectively with the opposing vertexes of the contact regions of the occlusal surfaces of the lower second premolars and first molars and the supporting cusps (supporting cuspals) of the upper first premolars and the second molars would not make contact with the flat occlusal surfaces of the opposing lower first premolars and second molars.

Moreover, the denture was similarly further prepared using an articulator so that during lateral movement of the lower jaw, the supporting cusps (supporting cuspals) of the upper second premolars and the first molars would make simultaneous contact respectively with the opposing vertexes of the contact regions of the occlusal surfaces of the lower second premolars and first molars (which correspond to the lingual-side edge on the working side and the buccal edge on the balancing side) and the supporting cusps (supporting cuspals) of the upper first premolars and the second molars would not make contact with the flat occlusal surfaces of the opposing lower first premolars and second molars.

Occlusal Adjustment

After the denture was affixed, the dentist made the following occlusal adjustments on the left and right upper and lower first premolars, second premolars, first molars, and second molars. Adjustment was made so that for the teeth, the left and right canines would make contact during lateral movement and the left and right central incisors would make contact during forward movement.

Furthermore, adjustment was made so that in centric occlusion, the supporting cusps (supporting cuspals) of the upper second premolars and first molars would properly make contact with the base of the contact region on the occlusal surface of the lower second preinolars and first molars and the supporting cusps of the upper first premolars and second molars would make slight contact with the occlusal surface formed on the lower first premolars and second molars.

Adjustment was also made so that during frontal movement of the lower jaw, the supporting cusps (supporting cuspals) of the upper second premolars and the first molars would make simultaneous contact respectively with the opposing vertexes of the contact regions of the occlusal surfaces of the lower second premolars and first molars and the supporting cusps (supporting cuspals) of the upper. first premolars and the second molars would not make contact with the flat occlusal surfaces of the opposing lower first premolars and second molars.

Finally, adjustment was made so that during lateral movement of the lower jaw, the supporting cusps (supporting cuspals) of the upper second premolars and the first molars would make simultaneous contact respectively with the opposing vertexes of the contact regions of the occlusal surfaces of the lower second premolars and first molars (which correspond to the lingual-side edge on the working side and the buccal edge on the balancing side) and the supporting cusps (supporting cuspals) of the upper first premolars and the second molars would not make contact with the flat occlusal surfaces of the opposing lower first premolars and second molars.

FIG. 12 shows an example of preferred occlusion attained using the above occlusal, adjustment. The occlusal paper seen in the figure was used to check occlusion of the left, right, upper, and lower teeth in centric occlusion and during forward and lateral movement. FIG. 12 shows that all molars make opposed contact with each other in centric occlusion, but spot contact is made by the following four pairs of teeth: the left and right first premolars and second molars of the upper and lower jaws. In contrast, the four pairs of teeth corresponding to the left and right second premolars and first molars of the upper and lower jaws made full occlusal contact, demonstrating the four point supporting configuration that includes mainly these four pairs of teeth.

During forward and lateral movement, it became clear that the left and right second premolars and first molars of the upper and lower jaws made full opposed contact while the left and right first premolars and second molars of the upper and lower jaws barely touched. This demonstrates the four point supporting mechanism that includes mainly the left and right second premolars and first molars of the upper and lower jaws during forward and lateral movement.

Results

A prominent improvement in the subjective symptoms claimed by the patient was noted with one adjustment performed after the denture was affixed. The dentist was able to make the adjustment quickly and easily. Over a two-month period, the patient was examined six times to check for changes in occlusion accompanying changes in the body and for improvement in subjective symptoms as well as to confirm that subjective symptoms had not recurred. Then, treatment was concluded. The treatment ameliorated the following subjective symptoms of the patient: headache, shoulder pain, stiff shoulders, knee pain, and tinnitus. A marked improvement was noted in the headache, shoulder pain, and stiffness of the shoulders symptoms.

Case 2

Patient: A 72-year-old female.

Symptoms: lumbago, hearing difficulties

False teeth:
  Upper jaw: All left and right teeth (14)
  Lower jaw: All left and right teeth (14)

Of these, the 16 false teeth corresponding to the upper and lower first premolars, second premolars, first molars, and second molars were the false teeth described in the above embodiments and shown in FIGS. 6–11. The others were known false teeth. The denture was prepared as described in case 1 using these false teeth.

Occlusal Adjustment

After the denture was affixed, the dentist made the occlusal adjustments as described in case 1 on the left and right upper and lower first premolars, second premolars, first molars, and second molars.

Results

A prominent improvement in the subjective symptoms claimed by the patient was noted with one adjustment performed after the denture was affixed. The dentist was able to make the adjustment quickly and easily. Over a two and half month period, the patient was examined seven times to check for changes in occlusion accompanying changes in the body and for improvement in subjective symptoms as well as to confirm that subjective symptoms had not recurred. Then, treatment was concluded. A marked improvement was noted in the lumbago and hearing difficulties.

Case 3

Patient: A 50-year-old female.

Symptoms: headache, stiff shoulders, shoulder pain, stiff neck, asthenopia

False teeth:
  Upper jaw: All teeth except for the right first premolar (13)
  Lower jaw: All teeth except for the right canine and the left lateral incisor and canine and second premolar (10)

Of these, the 16 false teeth corresponding to the upper and lower first premolars, second premolars, first molars, and second molars were the false teeth described in the above embodiments and shown in FIGS. 6–11. The others were known false teeth. The non-false teeth of the patient were her remaining teeth. The denture was prepared as described in case 1 using these false teeth.

Occlusal Adjustment

After the denture was affixed, the dentist made the occlusal adjustments as described in case 1 on the left and right upper and lower first premolars, second premolars, first molars, and second molars.

Results

A prominent improvement in the subjective symptoms claimed by the patient was noted with one adjustment performed after the denture was affixed. The dentist was able to make the adjustment quickly and easily. Over a one and half month period, the patient was examined four times to check for changes in occlusion accompanying changes in the body and for improvement in subjective symptoms as well as to confirm that subjective symptoms had not recurred. Then, treatment was concluded. A marked improvement was noted in the headache, stiff shoulders, shoulder pain, stiff neck, asthenopia symptoms.

Case 4

Patient: A 73-year-old male.

Symptoms: headaches, jaw pain, stiff shoulders, stiff neck, backaches, lumbago

False teeth:
  Upper jaw: All teeth except for the right second premolar (13)
  Lower jaw: All left and right teeth (14)

Of these, the 16 false teeth corresponding to the upper and lower first premolars, second premolars, first molars, and second molars were the false teeth described in the above embodiments and shown in FIGS. 6–11. The others were known false teeth. The non-false teeth(1) of the patient was her remaining teeth. The denture was prepared as described in case 1 using these false teeth.

Occlusal Adjustment

After the denture was affixed, the dentist made the occlusal adjustments as described in case 1 on the left and right upper and lower first premolars, second premolars, first molars, and second molars.

Results

A prominent improvement in the subjective symptoms claimed by the patient was noted with one adjustment performed after the denture was affixed. The dentist was able to make the adjustment quickly and easily. Over ten days, the patient was examined two times to check for changes in occlusion accompanying changes in the body and for improvement in subjective symptoms as well as to confirm that subjective symptoms had not recurred. Then, treatment was concluded. An improvement was noted in the stiff neck and headache. A marked improvement was noted in the stiff shoulders, backaches, and lumbago.

Case 5

Patient: A 53-year-old female.

Symptoms: headaches, jaw pain, stiff shoulders, shoulder pain, backaches, lumbago, asthenopia False teeth:

Upper jaw: All teeth except for the right central incisor, the left second premolar and first molar (11)

Lower jaw: All teeth except for the right central incisor, lateral incisor, canine and the left first molar (10)

Of these, the 16 false teeth corresponding to the upper and lower first premolars, second premolars, first molars, and second molars were the false teeth described in the above embodiments and shown in FIGS. 6–11. The others were known false teeth. The non-false teeth (7) of the patient were her remaining natural teeth. The denture was prepared as described in case 1 using these false teeth.

Occlusal Adjustment

After the denture was affixed, the dentist made the occlusal adjustments as described in case 1 on the left and right upper and lower first premolars, second premolars, first molars, and second molars.

Results

A prominent improvement in the subjective symptoms claimed by the patient was noted with one adjustment performed after the denture was affixed. The dentist was able to make the adjustment quickly and easily. Over ten days, the patient was examined two times to check for changes in occlusion accompanying changes in the body and for improvement in subjective symptoms as well as to confirm that subjective symptoms had not recurred. Then, treatment was concluded. An improvement was noted in the headaches, jaw pain, stiff shoulders, shoulder pain, backaches, lumbago and asthenopia symptoms. A marked improvement was noted in the headaches, jaw pain, stiff shoulders, shoulder pain and backaches symptoms.

The above cases are believed to confirm that the false teeth and dentures of the present teachings, whether worn by a patient as a full or partial denture, provide effective treatment mainly by balancing occlusal force. Thus, generalized conditions are prevented that might develop due to malocclusion and improve generalized conditions that occur due to malocclusion. Therefore, the above-described dentures provide excellent occlusal balance during mastication. Consequently, balanced occlusal force is provided by improving abnormalities in the center of occlusion, cuspal interference, and movement restrictions on the lower jaw, which are thought to cause malocclusion.

Representative Method of Making False Teeth

A representative example for making the false teeth of the present teachings will be described next. In the following working example, the ingredients shown in Tables 1 and 2 were used in the ratios given. A composite resin tooth 1 was made based on the composition shown in Table 1 and a composite resin tooth 2 was made based on the composition shown in Table 2. The second layer given in Tables 1 and 2 is the internal layer, as described above.

TABLE 1

| kind of layer | | components | composition (weight part) |
| --- | --- | --- | --- |
| the first layer | occlusal surface | copolymer of ethylmethacrylate and methylmethacrylate (40:60) | 46 |
| | | methylmethacrylate | 23 |
| | | cross-linking agent (triethylene-glycol dimethacrylate) | 10 |
| | | inorganic filler* | 21 |
| | | polymerization initiator (benzoyl peroxide) | 0.5 |
| second layer | intermediate layer | urethane dimethacrylate | 18 |
| | | cross-linking agent** | 8 |
| | | inorganic filler* | 74 |
| | | polymerization initiator (benzoyl peroxide) | 0.5 |
| third layer | base layer | polymethylmethacrylate | 67 |
| | | methylmethacrylate | 33 |
| | | polymerization initiator (benzoyl peroxide) | 0.5 |

*spherical silica (average diameter of 20 m)
**triethyleneglycol dimethacrylate

TABLE 2

| kind of layer | | components | composition (weight part) |
| --- | --- | --- | --- |
| the first layer | occlusal surface | polymethylmethacrylate | 67 |
| | | methylmetacrylate | 33 |
| | | polymerization initiator (benzoyl peroxide) | 0.5 |
| second layer | intermediate layer | urethane dimethacrylate | 32 |
| | | cross-linking agent** | 3 |
| | | inorganic filler* | 65 |
| | | polymerization initiator (benzoyl peroxide( ) | 0.5 |
| third layer | base layer | polymethylmethacrylate | 67 |
| | | methylmethacrylate | 33 |
| | | polymerization initiator (benzoyl peroxide) | 0.5 |

*spherical silica (average diameter of 5 m–50 m)
**triethylenglycol dimethacrylate The components of the layers given in the tables were prepared, the components were input into a mold with a tooth-shaped cavity starting with those of the first layer and ending with those of the third layer. This was heated at 100° C. for 10 minutes to produce the composite resin teeth 1 and 2. Moreover; the resin teeth 1 and 2 were aesthetically satisfactory.

The components of the first and second layers in Tables 1 and 2 were formed under conditions identical to those of the tooth formation above into molding A (that corresponded to the first layer of Table 1), molding B (that corresponded to the second layer of Table 1), molding C (that corresponded to the first layer of Table 2), and molding D (that corresponded to the second layer of Table 2). Each molding had a diameter of 15 mm and a thickness of 2 mm.

Testing using the Vickers hardness testing method of JIS Z2244 was performed on the moldings A–D. Testing was conducted with a load of 1 kg for 15 seconds. The results are shown in Table 3.

Moreover, the components of the first and second layers in Tables 1 and 2 were formed under conditions identical to those of the tooth formation above into molding E (that corresponded to the first layer of Table 1), molding F (that corresponded to the second layer of Table 1), molding G (that corresponded to the first layer of Table 2), and molding H (that corresponded to the second layer of Table 2). Each molding had a diameter of 120 mm and a thickness of 5 mm.

Wear-resistance testing based on JIS K7204 was performed on moldings E–H. The testing conditions were 300 rotations at 60 rpm at 23° C. using a CS17 grinding wheel and a testing load of 500 g. Table 3 shows the results of this testing as well.

TABLE 3

| Resin teeth | molding | Vickers hardness | amount of wear (mg) |
| --- | --- | --- | --- |
| 1 | 1st layer | 25.9 | 3.6 |
|   | 2nd layer | 98.8 | 0.5 |
| 2 | 1st layer | 20 | 4.9 |
|   | 2nd layer | 72.5 | 1 |

As is shown in Table 3, the hardness of the second layers of the resin teeth 1 and 2 was greater than that of the first layers. The amount of wear in the second layers was less than that of the corresponding first layers, and the wear resistance of the second layers was greater than that of the first layers.

Next, the resin teeth 1 and 2 were used as the lower second premolars and first molars (left and right) of the dentition of the denture shown in FIG. 5 to make two types of full dentures L and M. In the preparation of the full dentures, a resin tooth 3 that was a false tooth containing the ratio of ingredients of the first layer of the resin tooth 2 throughout and a resin tooth 4 that was a false tooth containing the first and second layers of the resin tooth 2 reversed and the third layer thereof unchanged were made under conditions similar to those used when forming the resin teeth 1 and 2. The resin tooth 3 was a conventional acrylic resin tooth and the resin tooth 4 was a conventional hard resin tooth. The false tooth marked with the triangle in the dentition of the denture in FIG. 5 is the resin tooth 3, and that marked with the square is the resin tooth 4.

Two types of full dentures O and P were formed as comparative examples using the resin teeth 3 and 4 for the lower second premolar and first molar shown in the denture in FIG. 5.

The four types of full dentures were affixed to different patients requiring full dentures, and a performance test under actual use was conducted. FIG. 4 shows the results of observations of grinding and discoloration of the surfaces of the lower second premolars and first molars while also showing the results of observations of occlusal stability in each patient over time.

During the first 30 days of wear of the dentures L and M, occlusion changed, but stable occlusion was achieved thereafter without occlusal adjustment by the dentist. This means that satisfactory occlusion occurred and was maintained for the individual patient about 30 days after the denture is affixed. This also indicates that use wears out the first layer, a pattern of wearing according to the individual user forms, and this is maintained by the second layer.

White grinding was satisfactory and no discoloration occurred in the resin tooth 3 of the second premolar and the first molar of the denture O, occlusion did not stabilize with use and actually changed unchecked. In the resin tooth 4 of the denture P, grinding was problematic, and discoloration readily occurred. Moreover, occlusal adjustment had to be repeatedly performed following affixing.

What is claimed is:

1. A denture comprising:
   a denture plate and
   at least one false tooth affixed to the denture plate, the at least one false tooth corresponding to at least one of an upper second premolar, an upper first molar, a lower second premolar or a lower first molar, wherein the following conditions are satisfied when the denture is implanted in a patient:
   (a) an imaginary plane passing through supporting cuspals of upper second premolars and supporting cuspals of upper first molars is parallel, or substantially parallel, to an occlusal plane,
   (b) an imaginary plane passing through bases of opposed-tooth contact regions formed on occlusal surfaces of lower second premolars and lower first molars is parallel, or substantially parallel, to the occlusal plane, wherein the opposed-tooth contact regions of the lower second premolars and the lower first molars have substantially concave surfaces and
   (c) in centric occlusion, the supporting cusps of the upper second premolars and supporting cusps of the upper first molars contact the bases of the respective opposed-tooth contact regions formed on the occlusal surfaces of the lower second premolars and the lower first molars.

2. A denture as in claim 1, wherein the following additional condition is satisfied when the denture is implanted in a patient:
   (d) an imaginary plane passing through a vertex of the opposed-tooth contact region formed on the occlusal surface of the lower second premolars and the lower

TABLE 4

| denture | type of false teeth | grinding | Discoloration (60 day) | occlusal stability | | | |
| --- | --- | --- | --- | --- | --- | --- | --- |
|   |   |   |   | 30 day | 60 day | 90 day | 300 day |
| M | resin teeth 1 | satisfactory | n.d. | change | Stabilized | stabilized | stabilized |
| N | resin teeth 2 | satisfactory | n.d. | change | Stabilized | stabilized | stabilized |
| O | resin teeth 3 | satisfactory | n.d. | change | change | change | change |
| P | resin teeth 4 | problematic | Detected | adjustment | adjustment | stabilized | stabilized | n.d.: not detected

As Table 4 shows, grinding in the resin teeth 1 and 2 of the lower second premolars and the first molars of the dentures L and M was satisfactory, and the dentist found occlusal adjustment to be easy. After the passage of 60 days, the resin teeth 1 and 2 had a surface color identical to that when they were affixed. There was no discoloration, and staining was not noted.

first molars is parallel, or substantially parallel, to the occlusal plane.

3. A denture as in claim 1, wherein the following additional condition is satisfied when the denture is implanted in a patient:
   (e) the supporting cusps of the upper second premolars and the supporting cusps of the upper first molars make simultaneous, or substantially simultaneous, contact in the opposed-tooth contact regions of the false tooth or teeth corresponding to the occlusal surface of the lower second premolars and the lower first molars.

4. A denture as in claim 1, wherein the opposed-tooth contact region formed on the occlusal surface of the false tooth or teeth of the denture further satisfies the following conditions when the denture is implanted in a patient:
(i) sagittal incisa guide angle≧sagittal condylar guide angle and
(ii) lateral incisal guide angle>sagittal condylar guide angle.

5. A denture as in claim 1, wherein the opposed-tooth contact region formed on the occlusal surface of the false tooth or teeth is smooth-surfaced.

6. A denture as in claim 1, wherein the denture comprises at least two false teeth corresponding to an upper first premolar and an upper second molar and wherein the following additional conditions are satisfied when the denture is implanted in a patient:
(a) the occlusal surface of the at least one false tooth is parallel, or substantially parallel, to the occlusal plane and
(b) an imaginary plane passing through the supporting cuspal or cuspals of the upper first premolar and the upper second molar is parallel, or substantially parallel, to the occlusal plane.

7. A denture as in claim 1, comprising false teeth corresponding to at least the upper and lower second premolars and the first molars, wherein:
the upper second premolars and first molars have an identical, or substantially identical, hardness,
the lower second premolars and first molars have an identical, or substantially identical, hardness, and
the lower second premolars and first molars have a hardness equal to or less than the hardness of the upper second premolars and first molars.

8. A denture according to claim 7, comprising false teeth corresponding to the upper and lower first premolars and second molars, wherein:
the upper second premolars and first molars have a hardness equal to or greater than the hardness of the upper first premolar and the second molar and
the lower second premolars and first molars have a hardness equal to or greater than the hardness of the lower first premolars and second molars.

9. A denture of claim 1, wherein the at least one false tooth comprises an exterior occlusal surface layer and an interior material supporting the exterior occlusal surface layer, wherein the interior material comprises at least a portion having a wear resistance and/or hardness greater than the wear resistance and/or hardness of the exterior occlusal surface layer, wherein the exterior occlusal surface layer comprises polyalkyl (meth)acrylate as a primary ingredient and the Vickers hardness of the exterior oclusal surface layer is between about 15 to 60 and wherein the Vickers hardness of at least a portion of the interior material is between about 25 to 200.

10. A denture as in claim 1, wherein the denture comprises at least two false teeth corresponding to an upper first premolar and an upper second molar and wherein the following additional conditions are satisfied when the denture is implanted in a patient:
(d) the occlusal surface of the at least one false tooth is parallel, or substantially parallel, to the occlusal plane,
(e) an imaginary plane passing through the supporting cuspal or cuspals of the upper first premolar and the upper second molar is parallel, or substantially parallel, to the occlusal plane,
(f) an imaginary plane passing through a vertex of the opposed-tooth contact region formed on the occlusal surface of the lower second premolars and the lower first molars is parallel, or substantially parallel, to the occlusal plane and
(g) the supporting cusps of the upper second premolars and the supporting cusps of the upper first molars make simultaneous, or substantially simultaneous, contact in the opposed-tooth contact regions of the false tooth or teeth corresponding to the occlusal surface of the lower second premolars and the lower first molars wherein the opposed-tooth contact region formed on the occlusal surface of the false tooth or teeth of the denture further satisfies the following conditions when implanted in a patient:
(i) sagittal incisal guide angle≧sagittal condylar guide angle and
(ii) lateral incisal guide angle>sagittal condylar guide angle wherein the opposed-tooth contact region formed on the occlusal surface of the false tooth or teeth is smooth-surfaced.

11. A denture as in claim 10, comprising false teeth corresponding to at least the upper and lower second premolars and the first molars, wherein:
the upper second premolars and first molars have an identical, or substantially identical, hardness,
the lower second premolars and first molars have an identical, or substantially identical, hardness, and
the lower second premolars and first molars have a hardness equal to or less than the hardness of the upper second premolars and first molars.

12. A denture according to claim 11, further comprising false teeth corresponding to second molars, wherein:
the upper second premolars and first molars have a hardness equal to or greater than the hardness of the upper first premolar and the second molar and
the lower second premolars and first molars have a hardness equal to or greater than the hardness of the lower first premolars and second molars.

13. A denture as in claim 12, wherein when the denture is implanted in a patent, the following arrangement is provided in centric occlusion:
supporting cuspals of the first premolars and the second molars are arranged at an identical height and
supporting cuspals of the second premolars and the first molars are arranged at an identical height and located below the supporting cuspals of the first premolars and the second molars.

14. A denture as in claim 13, wherein a line connecting the supporting cuspals of the first premolars and the second molars and a line connecting the supporting cuspals of the second premolars and the first molars are parallel, or substantially parallel, to the occlusal plane.

15. A denture of claim 14, wherein the at least one false tooth comprises an exterior occlusal surface layer and an interior material supporting the exterior occlusal surface layer, wherein the interior material comprises at least a portion having a wear resistance and/or hardness greater than the wear resistance and/or hardness of the exterior occlusal surface layer, wherein the exterior occlusal surface layer comprises polyalkyl (meth)acrylate as a primary ingredient and the Vickers hardness of the exterior occlusal surface layer is between about 15 to 60 and wherein the Vickers hardness of at least a portion of the interior material is between about 25 to 200.

16. A denture comprising a denture plate and a plurality of false teeth affixed to the denture plate corresponding to lower second premolars and/or lower first molars, wherein the following conditions are satisfied when the denture is implanted in a patient:
  (a) a first imaginary plane passing through bases of opposed-tooth contact regions formed on occlusal surfaces of the lower second premolars and the lower first molars is parallel, or substantially parallel, to the occlusal plane,
  (b) a second imaginary plane passing through distal edges of the opposed-tooth contact regions formed on the occlusal surfaces of the lower second premolars and the lower first molars is parallel, or substantially parallel, to the occlusal plane,
  wherein the opposed-tooth contact regions of the lower second premolars and the lower first molars have substantially concave surfaces.

17. A denture of claim 16, wherein the at least one false tooth comprises an exterior occlusal surface layer and an interior material supporting the exterior occlusal surface layer, wherein the interior material comprises at least a portion having a wear resistance and/or hardness greater than the wear resistance and/or hardness of the exterior occlusal surface layer, wherein the exterior occlusal surface layer comprises polyalkyl (meth)acrylate as a primary ingredient and the Vickers hardness of the exterior occlusal surface layer is between about 15 to 60 and wherein the Vickers hardness of at least a portion of the interior material is between about 25 to 200.

18. A false tooth adapted to be affixed to a denture, wherein the false tooth corresponds to a lower second premolar and/or a lower first molar, wherein the shape of a tooth contact region formed on an occlusal surface of the false tooth satisfies the following conditions:
  (a) sagittal incisal guide angle≧sagittal condylar guide angle and
  (b) lateral incisal guide angle>sagittal condylar guide angle.

19. A denture comprising a denture plate and at least one false tooth of claim 18 affixed to the denture plate.

20. A false tooth of claim 18, wherein the false tooth comprises an exterior occlusal surface layer and an interior material supporting the exterior occlusal surface layer, wherein the interior material comprises at least a portion having a wear resistance and/or hardness greater than the wear resistance and/or hardness of the exterior occlusal surface layer, wherein the exterior occlusal surface layer comprises polyalkyl (meth)acrylate as a primary ingredient and the Vickers hardness of the exterior occlusal surface layer is between about 15 to 60 and wherein the. Vickers hardness of at least a portion of the interior material is between about 25 to 200.

21. A denture comprising a denture plate and at least one false tooth affixed to the denture plate corresponding to lower first premolars, second premolars, first molars, and/or second molars, wherein bases of occlusal surfaces of the first premolars and second molars are parallel, or substantially parallel to an occlusal plane and bases of occlusal surfaces of the second premolars and first molars are parallel, or substantially parallel to the occlusal plane and located below the bases of the occlusal surfaces of the first premolars and second molars.

22. A denture comprising a denture plate and at least one false tooth affixed to the denture plate corresponding to upper first premolars, second premolars, first molars, and/or second molars, wherein when the denture is implanted in a patent, the following arrangement is provided in centric occlusion:
  supporting cuspals of the first premolars and the second molars are arranged at an identical height and
  supporting cuspals of the second premolars and the first molars are arranged at an identical height and located below the supporting cuspals of the first premolars and the second molars.

23. A denture as in claim 22, wherein a line connecting the supporting cuspals of the first premolars and the second molars and a line connecting the supporting cuspals of the second premolars and the first molars are parallel, or substantially parallel, to the occlusal plane.

24. A denture of claim 22, wherein the at least one false tooth comprises an exterior occlusal surface layer and an interior material supporting the exterior occlusal surface layer, wherein the interior material comprises at least a portion having a wear resistance and/or hardness greater than the wear resistance and/or hardness of the exterior occlusal surface layer, wherein the exterior occlusal surface layer comprises polyalkyl (meth)acrylate as a primary ingredient and the Vickers hardness of the exterior occlusal surface layer is between about 15 to 60 and wherein the Vickers hardness of at least a portion of the interior material is between about 25 to 200.

25. A denture comprising a denture plate and a plurality. of false teeth corresponding to a lower first premolar, second premolar, first molar, and/or second molar, wherein the shapes of opposed-tooth contact regions formed on occlusal surfaces of the second premolar and the lower first molar satisfy the following conditions when implanted in a patient:
  (a) sagittal incisal guide angle≧sagittal condylar guide angle and
  (b) lateral incisal guide angle>sagittal condylar guide angle and the shapes of opposed-tooth contact regions on occlusal surfaces of the first premolar and the second molar satisfy the following conditions when implanted in a patient:
  (a) sagittal incisal guide angle≧sagittal condylar guide angle and
  (b) lateral incisal guide angle>sagittal condylar guide angle or the shapes are sloped more gently than a shape satisfying the above conditions.

26. A denture of claim 25, wherein the at least one false tooth comprises an exterior occlusal surface layer and an interior material supporting the exterior occlusal surface layer, wherein the interior material comprises at least a portion having a wear resistance and/or hardness greater than the wear resistance and/or hardness of the exterior occlusal surface layer, wherein the exterior occlusal surface layer comprises polyalkyl (meth)acrylate as a primary ingredient and the Vickers hardness of the exterior occlusal surface layer is between about 15 to 60 and wherein the Vickers hardness of at least a portion of the interior material is between about 25 to 200.

27. In combination,
  a first false tooth corresponding to an upper second premolar, the first false tooth having lingual cuspals that provide a sole portion for opposed contact, wherein the lingual cuspals are partial spheres, a second false tooth corresponding to an upper first molar, the first false tooth having lingual cuspals that provide a sole portion for opposed contact, wherein the lingual cuspals are partial spheres, wherein the first false tooth and the second false tooth are connected.

28. A false tooth comprising an exterior occlusal surface layer and an interior material supporting the exterior occlusal surface layer, wherein the interior material comprises at least a portion having a wear resistance and/or hardness greater than the wear resistance and/or hardness of the exterior occlusal surface layer.

29. A false tooth as in claim 28, wherein the exterior occlusal surface layer comprises polyalkyl (meth)acrylate as a primary ingredient.

30. A denture comprising a dental plate and the false tooth of claim 29 affixed to the dental plate.

31. A false tooth according to claim 28, wherein the Vickers hardness of the exterior occlusal surface layer is between about 15 to 60.

32. A false tooth as in claim 31, wherein the exterior occlusal surface layer comprises polyalkyl (meth)acrylate as a primary ingredient.

33. A false. tooth according to claim 28, wherein the Vickers hardness of at least a portion of the interior material is between about 25 to 200.

34. A false tooth as in claim 33, wherein the exterior occlusal surface layer comprises polyalkyl (meth)acrylate as a primary ingredient.

35. A false tooth adapted to be affixed to a denture, wherein the false tooth corresponds to a lower second premolar and/or a lower first molar and an opposed-Tooth contact region formed on an occiusal surface of the false tooth has a substantially smooth, concave surface lacking bumps, wherein the false tooth comprises an exterior occlusal surface layer and an interior material supporting the exterior occlusal surface layer, wherein the interior material comprises at least a portion having a wear resistance and/or hardness greater than the wear resistance and/or hardness of the exterior occlusal surface layer, wherein the exterior occlusal surface layer comprises polyalkyl (math)acrylate as a primary ingredient and the Vickers hardness of the exterior occlusal surface layer is between about 15 to 60 and wherein the Vickers hardness of at least a portion of the interior material is between about 25 to 200.

36. A denture comprising a denture plate and at least one false tooth affixed to the denture plate corresponding to lower first premolars and/or second molars, wherein an occlusal surface of the at least one false tooth is a substantially flat surface and parallel, or substantially parallel, to an occlusal plane, wherein the at least one false tooth comprises an exterior occlusal surface layer and an interior material supporting the exterior occlusal surface layer, wherein the interior material comprises at least a portion having a wear resistance and/or hardness greater than the wear resistance and/or hardness of the exterior occlusal surface layer, wherein the exterior occlusal surface layer comprises polyalkyl (meth)acrylate as a primary ingredient and the Vickers hardness of the exterior occlusal surface layer is between about 15 to 60 arid wherein the Vickers hardness of at least a portion of the interior maternal is between about 25 to 200.

* * * * *